United States Patent
Morimoto et al.

(10) Patent No.: US 10,806,338 B2
(45) Date of Patent: Oct. 20, 2020

(54) ENDOSCOPE

(71) Applicant: FUJIFILM Corporation, Tokyo (JP)

(72) Inventors: Yasuhiko Morimoto, Kanagawa (JP); Shozo Iyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 393 days.

(21) Appl. No.: 15/886,843

(22) Filed: Feb. 2, 2018

(65) Prior Publication Data

US 2018/0242832 A1 Aug. 30, 2018

(30) Foreign Application Priority Data

Feb. 24, 2017 (JP) .................... 2017-033573

(51) Int. Cl.
| | |
|---|---|
| *A61B 1/00* | (2006.01) |
| *A61B 1/12* | (2006.01) |
| *A61B 1/273* | (2006.01) |
| *A61B 1/018* | (2006.01) |
| *A61B 1/06* | (2006.01) |
| *A61B 8/12* | (2006.01) |
| *A61B 8/00* | (2006.01) |

(52) U.S. Cl.
CPC .............. *A61B 1/126* (2013.01); *A61B 1/018* (2013.01); *A61B 1/0623* (2013.01); *A61B 1/273* (2013.01); *A61B 8/12* (2013.01); *A61B 8/445* (2013.01); *A61B 8/4494* (2013.01)

(58) Field of Classification Search
CPC .................... A61B 1/00098; A61B 1/00091
USPC ....................................................... 600/157
See application file for complete search history.

(56) References Cited

U.S. PATENT DOCUMENTS 7,771,349 B2 8/2010 Kohno
2015/0173711 A1* 6/2015 Hiraoka ............... A61B 8/4494
600/466

FOREIGN PATENT DOCUMENTS

| JP | S552408 | 1/1980 |
| JP | S552408 A * | 1/1980 |
| JP | H0235701 | 3/1990 |
| JP | H0266511 | 3/1990 |
| JP | H05103757 | 4/1993 |

(Continued)

OTHER PUBLICATIONS

"Office Action of Japan Counterpart Application," dated Feb. 27, 2020, with English translation thereof, p. 1-p. 8.

*Primary Examiner* — Alexandra L Newton
*Assistant Examiner* — Rynae Boler
(74) *Attorney, Agent, or Firm* — JCIPRNET (57) ABSTRACT

An endoscope includes an insertion part that includes a distal end and a proximal end, and a distal-end-portion body that is provided on a distal end side of the insertion part and formed with a treatment tool outlet from which a treatment tool is led out. The distal-end-portion body includes an observation window, a nozzle that ejects washing water to the observation window, a standing base that is disposed in a standing base-housing portion adjacent to the treatment tool outlet and is rotationally moved between a standing position and a falling position, and a guide wall that is disposed at a position facing the nozzle with the observation window interposed therebetween and guides the washing water to the standing base-housing portion. Washing water, which has been ejected from the nozzle and has passed the observation window, is guided to the standing base-housing portion by the guide wall.

12 Claims, 8 Drawing Sheets

(56) References Cited

FOREIGN PATENT DOCUMENTS

| | | | |
|---|---|---|---|
| JP | 05123285 A | * | 5/1993 |
| JP | H08173376 | | 7/1996 |
| JP | 2001286434 | | 10/2001 |
| JP | 2005287593 | | 10/2005 |
| JP | WO-2013132684 A1 | * | 9/2013 |
| WO | 2013132684 | | 9/2013 |

* cited by examiner

ENDOSCOPE

CROSS-REFERENCE TO RELATED APPLICATIONS

The present application claims priority under 35 U.S.C. § 119 to Japanese Patent Application No. 2017-033573, filed on Feb. 24, 2017. Each of the above application(s) is hereby expressly incorporated by reference, in its entirety, into the present application.

BACKGROUND OF THE INVENTION

1. Field of the Invention

The present invention relates to an endoscope including a standing base.

2. Description of the Related Art

An endoscope includes an observation window that is provided at a distal end portion of an endoscope insertion part. The observation window is provided with an imaging unit that is used to obtain an optical image. Signals, which are output from the imaging unit, are processed, so that the image of the inside of a body cavity can be observed through a monitor or the like.

Since the distal end portion of the endoscope insertion part is inserted into a body cavity, body fluid and blood may adhere to the observation window during the use of the endoscope. Various structures are proposed to wash the observation window.

JP1980-002408A (JP-S55-002408A) discloses an endoscope including a fluid guide wall that changes the flow direction of fluid to be ejected from a nozzle toward an objective lens.

JP1996-173376A (JP-H08-173376A) discloses an endoscope in which a forceps outlet in which a standing base is provided and an observation window are arranged side by side, a nozzle for washing the observation window is inclined so as to be directed to the forceps outlet, and the periphery of the observation window is formed of an inclined surface inclined toward the forceps outlet.

WO2013/132684A discloses an endoscope in which a convex portion is provided at a boundary portion between an illumination lens and an objective lens. Water, which is blown off by gas ejected from a nozzle, is made to flow to both sides by the convex portion, so that the return of water to the objective lens is prevented.

SUMMARY OF THE INVENTION

For example, a duodenoscope, an ultrasonic endoscope, and the like are known as an endoscope that includes a standing base adjusting the protruding angle of a treatment tool. In a duodenoscope, a guide wire, a contrast tube, and the like are inserted and a procedure, such as endoscopic retrograde cholangiopancreatography (ERCP), is performed. Further, in an ultrasonic endoscope, a puncture needle for ultrasonic waves is inserted and a procedure, such as fine needle aspiration cytology (FNA), is performed.

Incidentally, while the procedures using the duodenoscope and the ultrasonic endoscope are performed, mucus, blood, a contrast medium, and the like may adhere to the periphery of the standing base. Since mucus, blood, a contrast medium, and the like adhering to the periphery of the standing base are fixed in a case in which a procedure time is long, there is a problem that the operating resistance of the standing base is made larger than that in an initial state. Further, in a case in which a contrast medium is solidified in a treatment tool outlet and a treatment tool channel, there is a problem that the insertion resistance of a treatment tool is made larger than that in an initial state.

Since washing water is ejected toward the observation window from the nozzle in the endoscopes disclosed in JP1980-002408A (JP-S55-002408A), JP1996-173376A (JP-H08-173376A), and WO2013/132684A, it is difficult to reliably wash the periphery of the standing base.

The invention has been made in consideration of the above-mentioned circumstances, and an object of the invention is to provide an endoscope of which a standing base can be washed.

An endoscope according to a first aspect comprises an insertion part that includes a distal end and a proximal end, and a distal-end-portion body that is provided on a distal end side of the insertion part and formed with a treatment tool outlet from which a treatment tool is led out. The distal-end-portion body includes an observation window, a nozzle that ejects washing water to the observation window, a standing base that is disposed in a standing base-housing portion adjacent to the treatment tool outlet and is rotationally moved between a standing position and a falling position, and a guide wall that is disposed at a position facing the nozzle with the observation window interposed therebetween and guides the washing water to be ejected from the nozzle to the standing base-housing portion.

An endoscope according to a second aspect comprises an insertion part that includes a distal end and a proximal end, and a distal-end-portion body that is provided on a distal end side of the insertion part and formed with a treatment tool outlet from which a treatment tool is led out. The distal-end-portion body includes an observation window, a nozzle that ejects washing water to the observation window, a standing base that is disposed in a standing base-housing portion adjacent to the treatment tool outlet and is rotationally moved between a standing position and a falling position, and a guide wall that is disposed between the observation window and the nozzle and guides a part of the washing water to be ejected from the nozzle to the standing base-housing portion.

According to a third aspect, in the endoscope, the standing base-housing portion is formed by a pair of walls including wall surfaces facing each other with the standing base interposed therebetween, one wall of the pair of walls includes a flat surface continuously connected to the wall surface, and the observation window and the nozzle are disposed on the flat surface.

According to a fourth aspect, in the endoscope, the guide wall is disposed on the flat surface.

According to a fifth aspect, in the endoscope, the flat surface is formed of a parallel surface that is parallel to an axial direction of the distal-end-portion body.

According to a sixth aspect, in the endoscope, the flat surface is formed of an inclined surface that is inclined with respect to an axial direction of the distal-end-portion body.

According to a seventh aspect, in the endoscope, the nozzle is disposed closer to a distal end side of the distal-end-portion body than the observation window and ejects the washing water toward a proximal end side of the distal-end-portion body.

According to an eighth aspect, the endoscope further comprises an ultrasound transducer that is provided on a distal end side of the distal-end-portion body.

According to a ninth aspect, the endoscope further comprises a port that is provided on the wall surface of the one wall and ejects the washing water, and a branch pipe line that connects a fluid pipe line connected to the nozzle to the port.

According to a tenth aspect, in the endoscope, the wall surface of the other wall is positioned on an extension of an ejection direction of the washing water to be ejected from the port in a state in which the standing base is in the falling position.

According to the invention, the periphery of a standing base of an endoscope can be washed.

DESCRIPTION OF THE PREFERRED EMBODIMENTS

Preferred embodiments of the invention will be described below with reference to the accompanying drawings. The invention will be described using the following preferred embodiments. The invention can be modified by various methods without departing from the scope of the invention, and embodiments other than the embodiments can be used. Accordingly, all modifications within the scope of the invention are included in the claims.

First Embodiment

Figure 1:
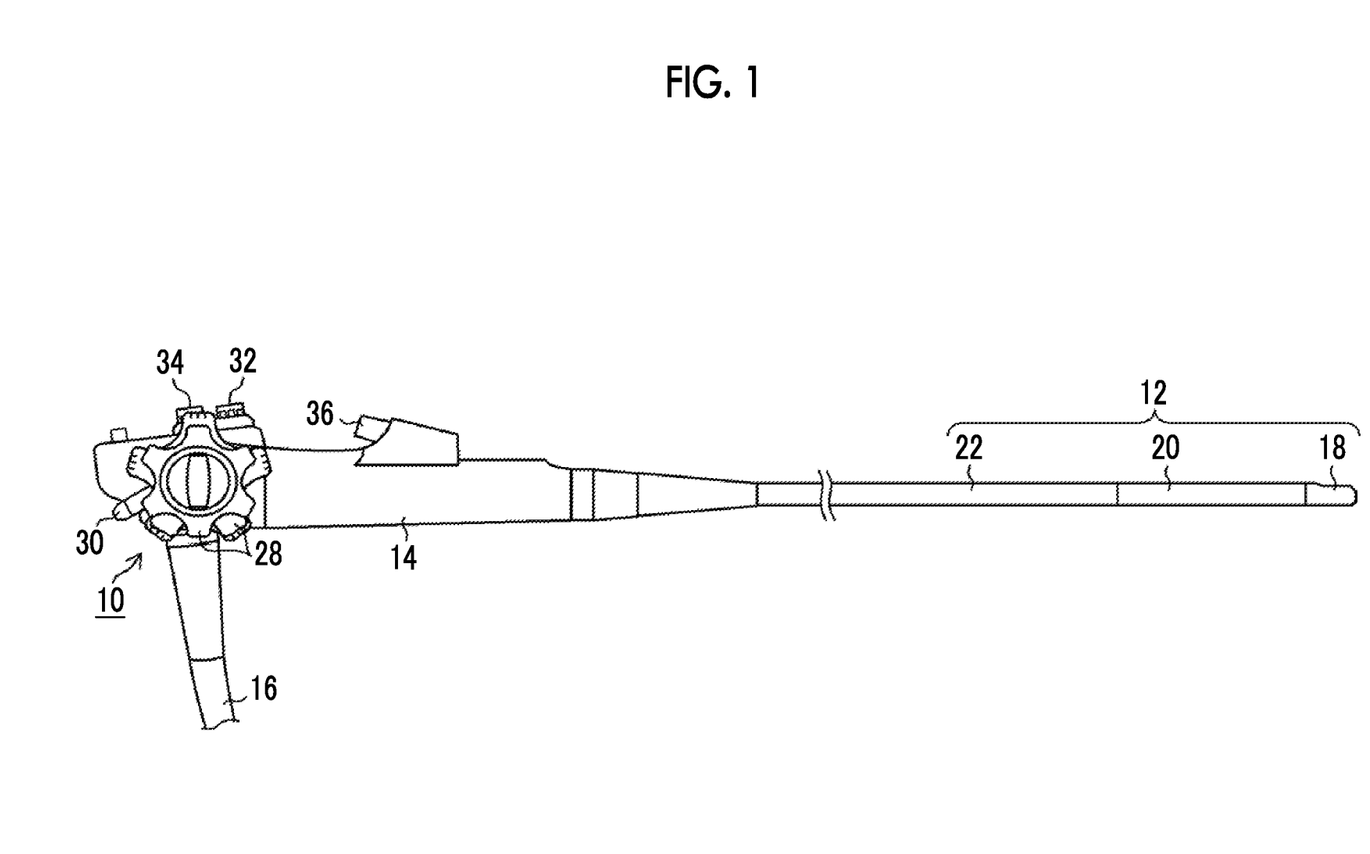
FIG. 1 is a diagram showing the structure of the entire endoscope.
Figure 2:
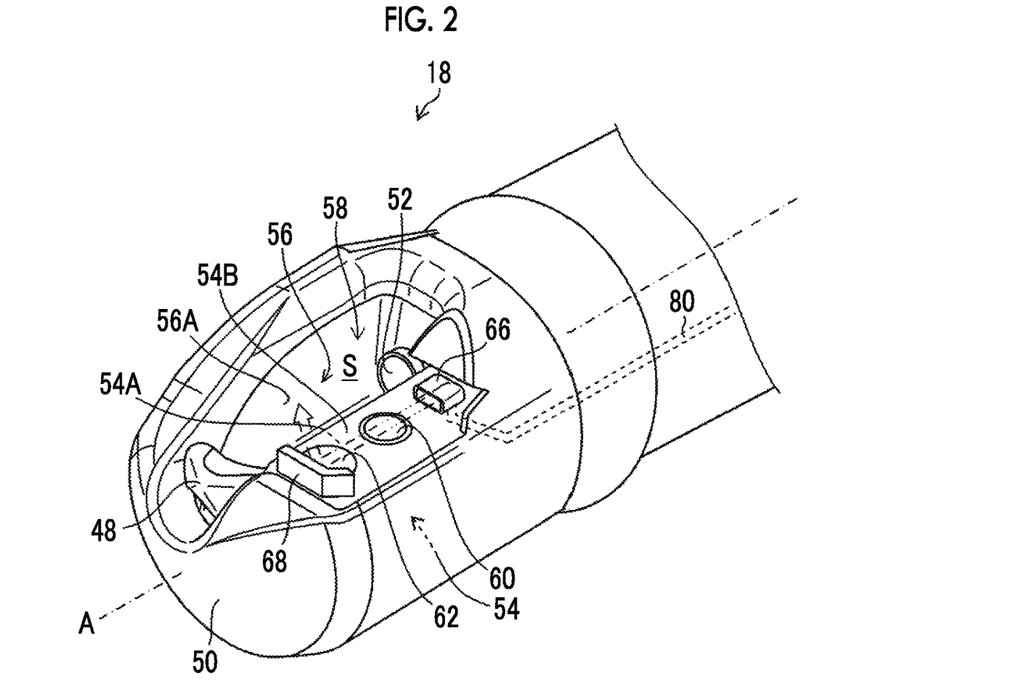
FIG. 2 is an enlarged perspective view of a distal-end-portion body of an endoscope according to a first embodiment.

Endoscopes according to the embodiments will be described below with reference to the accompanying drawings. FIG. 1 is a diagram showing the structure of the entire endoscope 10. FIG. 2 is an enlarged perspective view of a distal-end-portion body 18 of an endoscope according to a first embodiment.

The endoscope 10 includes an insertion part 12 that is to be inserted into the body of an examinee and includes a distal end and a proximal end, an operation unit 14 that is connected to the proximal end side of the insertion part 12, and a universal cord 16 that is connected to the operation unit 14. The endoscope 10 is connected to a light source device, an imaging processing device, and an air/water supply device, which are not shown, through the universal cord 16.

As shown in FIG. 1, the insertion part 12 includes a distal-end-portion body 18, a bendable portion 20, and a soft portion 22 in this order from the distal end side. The distal-end-portion body 18 is composed of a hard member in a substantially cylindrical shape. The bendable portion 20 is connected to the proximal end side of the distal-end-portion body 18. The soft portion 22 connects the proximal end side of the bendable portion 20 to the distal end side of the operation unit 14. The soft portion 22 has a small diameter and a long length and has flexibility. The operation unit 14 includes an angle knob 28 that is operated to vertically and laterally bend the bendable portion 20 of the insertion part 12, a standing operation lever 30 that is operated to rotationally move a standing base 48 (see FIG. 2), an air/water supply button 32 that is used to perform an air/water supply operation, and a suction button 34 that is used to perform a suction operation. Further, a treatment tool insertion opening 36 protrudes on the distal end side of the operation unit 14 so that various treatment tools are inserted into a treatment tool channel (not shown).

The endoscope shown in FIG. 2 is a side-viewing endoscope used as, for example, a duodenoscope and the distal-end-portion body 18 shown in FIG. 2 shows the structure of the side-viewing endoscope.

As shown in FIG. 2, the distal-end-portion body 18 includes a treatment tool outlet 52 that is provided on the proximal end side thereof. A space S, which forms a standing base-housing portion, is formed by a pair of walls 54 and 56 that includes wall surfaces 54A and 56A facing each other and is disposed so as to be spaced apart from each other. The space S is adjacent to the treatment tool outlet 52. The standing base 48 is disposed on the front side of the treatment tool outlet 52 so as to be spaced apart from the treatment tool outlet 52, and is housed in the space S. The front side of the treatment tool outlet 52 means a position closer to the distal end than the treatment tool outlet 52. An opening 58 is formed in the space S, and the space S is opened toward a standing position of the standing base 48 through the opening 58. In the first embodiment shown in FIG. 2, the standing base 48 is in a state in which the standing base 48 is in a falling position. As long as the pair of walls 54 and 56 can form the space S that can house the standing base 48, the pair of walls 54 and 56 may be connected to each other on the proximal end side of the distal-end-portion body 18.

In the first embodiment, the distal-end-portion body 18 is covered with a cap 50. The cap 50 is made of an elastic material, for example, fluororubber. In the endoscope 10, the cap 50 is attachably and detachably mounted on the distal-end-portion body 18. The cap 50 may be made of a polysulfone resin and may be fixed to the distal-end-portion body 18 by adhesion or the like.

The standing base 48 is rotationally moved between a standing position and a falling position by the operation of the standing operation lever 30. The standing base 48 is connected to the standing lever through a rotating shaft (not shown) with the other wall 56 interposed therebetween. A distal end portion of an operation wire is connected to a distal end of the standing lever. One end of the operation wire is connected to the standing lever, and the other end of the operation wire is inserted into the insertion part 12 and is connected to the standing operation lever 30 of the operation unit 14. The operation wire is pushed and pulled by the operation of the standing operation lever 30, so that the rotating shaft is rotated through the standing lever. The standing base 48 is rotated by the rotation of the rotating shaft, so that the standing base 48 is operated to stand and fall. A standing-base-standing mechanism, which rotates the rotating shaft, is not limited to a mechanism that pushes and pulls a standing lever by an operation wire.

A treatment tool (not shown), which is to be inserted from the treatment tool insertion opening 36 of the operation unit 14, is led out from the treatment tool outlet 52. The treatment tool passes through the space S, is led out from the opening 58, and is inserted into the body of an examinee. The lead-out direction of the treatment tool is changed by the standing base 48.

In the first embodiment, one wall 54 of the pair of walls 54 and 56 is provided with a flat surface 54B that is continuously connected to the wall surface 54A.

The flat surface 54B of the wall 54 is formed of a parallel surface substantially parallel to an axial direction A of the distal-end-portion body 18. Substantially parallel includes parallel. A normal direction of the flat surface 54B is substantially orthogonal to the axial direction A. An illumination window 62, an observation window 60, and a nozzle 66 are arranged toward the proximal end side from the distal end side on the flat surface 54B of the distal-end-portion body 18 so as to be substantially parallel to the axial direction A. The axial direction A of the distal-end-portion body 18 corresponds to the central axis of the insertion part 12 in a longitudinal direction. The axial direction A of the distal-end-portion body 18 does not necessarily need to correspond to the central axis of the insertion part 12 in the longitudinal direction. For example, the axial direction A of the distal-end-portion body 18 may be parallel to the central axis of the insertion part 12 in the longitudinal direction and may be shifted in a direction orthogonal to the central axis of the insertion part 12.

The nozzle 66 is disposed on the flat surface 54B so that the ejection direction of washing water and gas to be ejected from the nozzle 66 is directed to the observation window 60 and the illumination window 62. An air/water supply pipe line 80, which is a fluid pipe line, is connected to the nozzle 66. Any one of washing water and gas is ejected toward the observation window 60 from the nozzle 66 by the operation of the air/water supply button 32 of the operation unit 14.

In the first embodiment, a guide wall 68, which protrudes from the flat surface 54B, is disposed on the flat surface 54B on which the nozzle 66 is disposed. It is preferable that the height of the guide wall 68 is larger than the height of the observation window 60 and the height of the illumination window 62. The guide wall 68 is disposed at a position facing the nozzle 66 with the observation window 60 and the illumination window 62 interposed therebetween. In the first embodiment, the observation window 60 and the illumination window 62 are disposed between the nozzle 66 and the guide wall 68 as shown in FIG. 2. The guide wall 68 may be disposed at a position facing the nozzle 66 with at least the observation window 60 interposed therebetween. Accordingly, the guide wall 68 may be disposed between the observation window 60 and the illumination window 62. The guide wall 68 may be formed integrally with the flat surface 54B of the wall 54, or may be formed separately from the wall 54 and be fixed to the flat surface 54B by an adhesive or the like.

Next, the action of the structure will be described. As shown in FIG. 2, washing water is ejected toward the observation window 60 and the illumination window 62 from the nozzle 66 provided on the flat surface 54B as shown by an arrow by the operation of the air/water supply button 32 of the operation unit 14. Washing water passes the surface of the observation window 60 and the surface of the illumination window 62, and washes the surface of the observation window 60 and the surface of the illumination window 62.

Since the guide wall 68 is disposed at a position facing the nozzle 66 with the observation window 60 and the illumination window 62 interposed therebetween, washing water having passed the surface of the observation window 60 and the surface of the illumination window 62 collides with the guide wall 68. Washing water, which has collided with the guide wall 68, is guided to the space S, which is a standing base-housing portion, by the guide wall 68 and is guided toward the standing base 48. The standing base 48 is washed with washing water.

In the first embodiment, the guide wall 68 has a bent shape in top view. As a result, the guide wall 68 has two angles at a bent position. The guide wall 68 is formed substantially orthogonal to the axial direction A on the side closer to the space S than the bent position. The guide wall 68 is formed to be inclined in a direction toward the nozzle 66 on the side opposite to the space S from the bent position. Since this structure is employed, the guidance of washing water, which has passed the observation window 60, to the side opposite to the space S can be suppressed.

As long as the guide wall 68 can guide washing water, which has passed the observation window 60, to the space S, the shape of the guide wall 68 is not particularly limited. The guide wall 68 may have a linear shape in top view, or may have the shape of a curve, such as the shape of an arc shape, the shape of an elliptical arc, or the shape of a parabola in top view. In a case in which the guide wall 68 has the shape of a curve, it is preferable that the guide wall 68 is disposed so that the nozzle 66 is positioned inside the curved guide wall 68. The guidance of washing water, which has passed the observation window 60, to the side opposite to the space S can be suppressed.

Washing water, which flows into the space S, washes the standing base 48. Washing water, which washes the standing base 48, is sucked from the treatment tool outlet 52 by the operation of the suction button 34 of the operation unit 14 and is removed from the space S. The inside of the treatment tool channel can be washed with washing water that is sucked from the treatment tool outlet 52.

Washing water adhering to the observation window 60 can be blown off by gas to be ejected from the nozzle 66.

Second Embodiment

An endoscope according to a second embodiment will be described with reference to FIG. 3. There is a case where the same components as the components of the endoscope according to the first embodiment are denoted by the same reference numerals as the reference numerals of the first embodiment and the description thereof are omitted.

Figure 3:
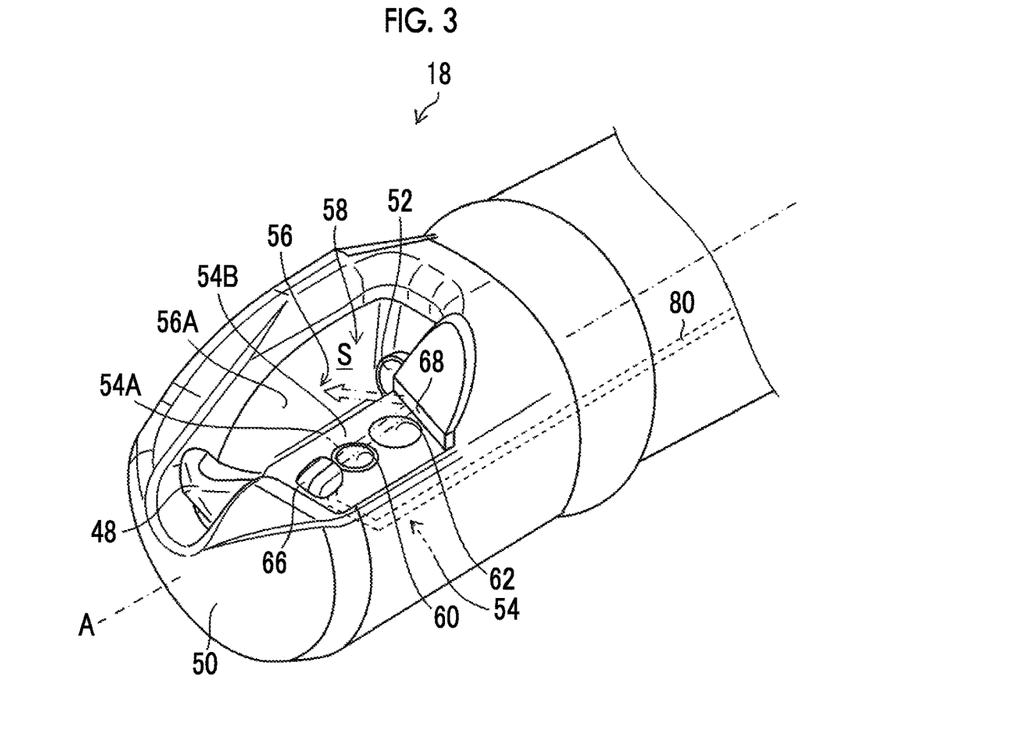
FIG. 3 is an enlarged perspective view of a distal-end-portion body of an endoscope according to a second embodiment.

The endoscope shown in FIG. 3 is a side-viewing endoscope used as, for example, a duodenoscope and a distal-end-portion body 18 shown in FIG. 3 shows the structure of the side-viewing endoscope.

As shown in FIG. 3, the distal-end-portion body 18 includes a treatment tool outlet 52 that is provided on the proximal end side thereof. A space S, which forms a standing base-housing portion, is formed by a pair of walls 54 and 56 that includes wall surfaces 54A and 56A facing each other and is disposed so as to be spaced apart from each other. The space S is adjacent to the treatment tool outlet 52. A standing base 48 is disposed on the front side of the treatment tool outlet 52 so as to be spaced apart from the treatment tool outlet 52, and is housed in the space S. An opening 58 is formed in the space S, and the space S is opened toward a standing position of the standing base 48 through the opening 58. In the second embodiment shown in FIG. 3, the standing base 48 is in a state in which the standing base 48 is in a falling position. Further, the distal-end-portion body 18 is covered with a cap 50.

Even in the second embodiment, one wall 54 of the pair of walls 54 and 56 is provided with a flat surface 54B that is continuously connected to the wall surface 54A.

The endoscope according to the second embodiment shown in FIG. 3 is different from the endoscope according to the first embodiment in terms of the arrangement of an observation window 60, an illumination window 62, a nozzle 66, and a guide wall 68. As shown in FIG. 3, the nozzle 66, the observation window 60, the illumination window 62, and the guide wall 68 are arranged toward the proximal end side from the distal end side on the flat surface 54B, which is a parallel surface of the distal-end-portion body 18, so as to be substantially parallel to an axial direction A. The guide wall 68 is disposed at a position facing the nozzle 66 with the observation window 60 and the illumination window 62 interposed therebetween. Accordingly, in the second embodiment, the nozzle 66 is disposed on the distal end side of the distal-end-portion body 18 and ejects washing water toward the proximal end side.

The nozzle 66 is connected to an air/water supply pipe line 80. In the second embodiment, the guide wall 68 includes a part of the cap 50. The guide wall 68 is not limited to the shape shown in FIG. 3.

The guide wall 68 has a linear shape in the second embodiment. However, the guide wall 68 is not limited thereto and may have a bent shape or the shape of a curve. It is preferable that the shape of the guide wall 68 is a shape that allows washing water having passed the observation window 60 not to be guided to the side opposite to the space S.

Next, the action of the structure will be described. As shown in FIG. 3, washing water is ejected toward the observation window 60 and the illumination window 62 from the nozzle 66 provided on the flat surface 54B as shown by an arrow by the operation of the air/water supply button 32 of the operation unit 14. Washing water, which has passed the surface of the observation window 60 and the surface of the illumination window 62, collides with the guide wall 68. Washing water, which has collided with the guide wall 68, is guided to the space S, which is a standing base-housing portion, by the guide wall 68 and is guided toward the standing base 48. The standing base 48 is washed with washing water. In the second embodiment, washing water is ejected toward the proximal end side from the nozzle 66 and is guided to the space S by the guide wall 68. Accordingly, washing water can be efficiently supplied to the rotating shaft of the standing base 48 and the treatment tool outlet 52. It is preferable that a large amount of washing water is supplied to a portion required to be washed.

Washing water, which flows into the space S, is sucked from the treatment tool outlet 52 by the operation of the suction button 34 of the operation unit 14 and is removed from the space S. The inside of the treatment tool channel can be washed with washing water that is sucked from the treatment tool outlet 52.

Washing water adhering to the observation window 60 can be blown off by gas to be ejected from the nozzle 66.

Third Embodiment

An endoscope according to a third embodiment will be described with reference to FIG. 4. There is a case where the same components as the components of the endoscopes according to the first and second embodiments are denoted by the same reference numerals as the reference numerals of the first and second embodiments and the description thereof are omitted.

Figure 4:
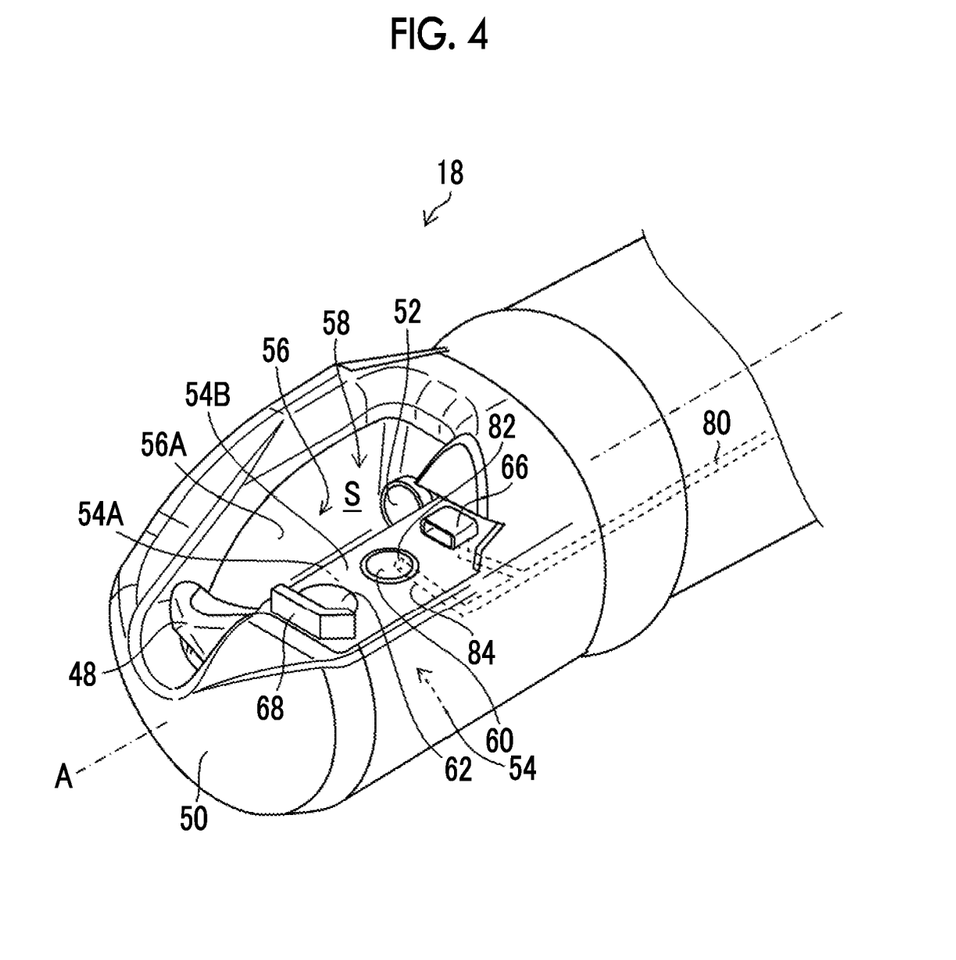
FIG. 4 is an enlarged perspective view of a distal-end-portion body of an endoscope according to a third embodiment.

The endoscope according to a third embodiment shown in FIG. 4 is a side-viewing endoscope used as, for example, a duodenoscope and a distal-end-portion body 18 shown in FIG. 4 shows the structure of the side-viewing endoscope.

As shown in FIG. 4, the distal-end-portion body 18 includes a treatment tool outlet 52 that is provided on the proximal end side thereof. A space S, which forms a standing base-housing portion, is formed by a pair of walls 54 and 56 that includes wall surfaces 54A and 56A facing each other and is disposed so as to be spaced apart from each other. The space S is adjacent to the treatment tool outlet 52. A standing base 48 is disposed on the front side of the treatment tool outlet 52 so as to be spaced apart from the treatment tool outlet 52, and is housed in the space S. An opening 58 is formed in the space S, and the space S is opened toward a standing position of the standing base 48 through the opening 58. In the third embodiment shown in FIG. 4, the standing base 48 is in a state in which the standing base 48 is in a falling position. Further, the distal-end-portion body 18 is covered with a cap 50.

As in the endoscope according to the first embodiment, in the endoscope according to the third embodiment shown in FIG. 4, an illumination window 62, an observation window 60, and a nozzle 66 are arranged toward the proximal end side from the distal end side on a flat surface 54B of the distal-end-portion body 18 so as to be substantially parallel to an axial direction A. A guide wall 68 is disposed on the flat surface 54B, on which the nozzle 66 is disposed, at a position facing the nozzle 66 with the observation window 60 and the illumination window 62 interposed therebetween. The nozzle 66 is connected to an air/water supply pipe line 80.

In the third embodiment shown in FIG. 4, the wall surface 54A of one wall 54 is provided with a port 82 that ejects washing water. A branch pipe line 84, which connects the air/water supply pipe line 80 to the port 82, is provided. The port 82 is an opening provided on the wall surface 54A.

Next, the action of the structure will be described. As shown in FIG. 4, washing water is supplied to the air/water supply pipe line 80 by the operation of the air/water supply button 32 of the operation unit 14. A part of washing water, which is supplied to the air/water supply pipe line 80, is ejected toward the space S from the port 82 through the branch pipe line 84.

The rest of the washing water is ejected toward the observation window 60 and the illumination window 62 from the nozzle 66, which is provided on the flat surface 54B, as shown by an arrow. Washing water having passed the surface of the observation window 60 and the surface of the illumination window 62 collides with the guide wall 68. Washing water, which has collided with the guide wall 68, is guided to the space S, which is a standing base-housing portion, by the guide wall 68 and is guided toward the standing base 48. Washing water, which flows in the branch pipe line 84, is ejected toward the standing base 48 from the port 82. The standing base 48 is washed with washing water that is guided by the guide wall 68 and washing water that is ejected from the port 82.

The wall surface 54A is preferably provided with the port 82 so that the wall surface 56A of the other wall 56 is positioned on the extension of the ejection direction of washing water to be ejected from the port 82 in a state in which the standing base 48 is in the falling position. Accordingly, the side surface of the standing base 48 facing the other wall 56 can be washed efficiently in a state in which the standing base 48 is in the falling position. It is preferable that the side surface of the standing base 48 is positioned on the extension of the ejection direction of washing water to be ejected from the port 82 in a state in which the standing base 48 is in the standing position. Accordingly, the side surface of the standing base 48 facing one wall 54 can be washed efficiently in a state in which the standing base 48 is in the standing position.

Washing water, which flows into the space S, is sucked from the treatment tool outlet 52 by the operation of the suction button 34 of the operation unit 14 and is removed from the space S. The inside of the treatment tool channel can be washed with washing water that is sucked from the treatment tool outlet 52. Washing water adhering to the observation window 60 can be blown off by gas to be ejected from the nozzle 66.

A side-viewing endoscope of which the flat surface 54B on which the observation window 60 and the nozzle 66 are disposed is a parallel surface parallel to the axial direction A has been described in each of the first to third embodiments. However, the structure of the endoscope is not limited to a side-viewing endoscope. For example, the guide wall 68 can also be disposed even in an oblique-viewing endoscope of which the flat surface 54B on which the observation window 60 and the nozzle 66 are disposed is formed of an inclined surface inclined with respect to the axial direction A of the distal-end-portion body 18. In a case in which the guide wall 68 is disposed in the oblique-viewing endoscope, washing water to be ejected from the nozzle 66 can be guided to the space S housing the standing base 48. Accordingly, the periphery of the standing base 48 and the treatment tool channel can be washed.

Fourth Embodiment

An endoscope 10 according to a fourth embodiment will be described with reference to FIGS. 5 to 8. There is a case where the same components as the components of the endoscopes 10 according to the first to third embodiments are denoted by the same reference numerals as the reference numerals of the first to third embodiments and the description thereof are omitted. The endoscope 10 according to the fourth embodiment is an ultrasonic endoscope that includes an ultrasound probe provided on the distal end side of a distal-end-portion body 18. The endoscope 10 according to the fourth embodiment includes a side-viewing endoscope and an oblique-viewing endoscope. The ultrasound probe of the distal-end-portion body 18 includes a plurality of ultrasound transducers.

Figure 5:
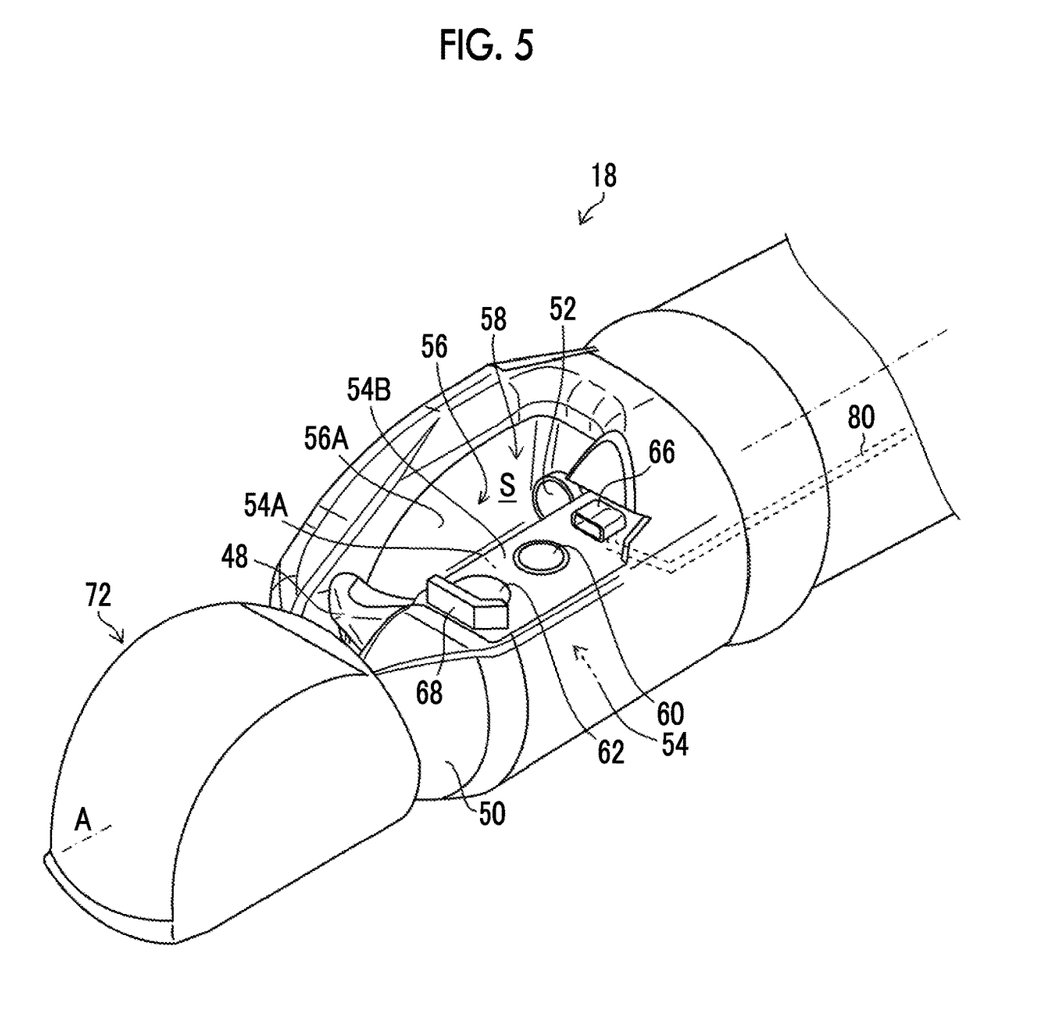
FIG. 5 is an enlarged perspective view of a distal-end-portion body of an endoscope according to a fourth embodiment.

As shown in FIG. 5, an ultrasound probe 72 is disposed on the distal end side of the distal-end-portion body 18 of the endoscope 10. The ultrasound probe 72 includes a curved surface that is curved outward in a convex shape toward the distal end side from the proximal end side thereof. The curved surface forms the outer surface of an acoustic lens. The ultrasound probe 72 includes a plurality of ultrasound transducers (not shown) that transmit and receive ultrasonic waves. The plurality of ultrasound transducers are arranged in an arc shape along the outer surface of the acoustic lens on the inside of the acoustic lens. Further, an ultrasound image (tomographic image) can be acquired by the ultrasound probe 72.

The endoscope according to the fourth embodiment shown in FIG. 5 includes a treatment tool outlet 52, a space S that forms a standing base-housing portion, a standing base 48 that is housed in the space S, and a pair of walls 54 and 56 that includes wall surfaces 54A and 56A as in the endoscope according to the first embodiment, except for the ultrasound probe 72. The space S includes an opening 58, and is opened toward the ultrasound probe 72 through the opening 58 in a case in which the distal-end-portion body 18 is viewed from the distal end side. A guide wall 68, an illumination window 62, an observation window 60, and a nozzle 66 are arranged along an axial direction A toward the proximal end side from the distal end side on a flat surface 54B that is continuously connected to the wall surface 54A. The flat surface 54B shown in FIG. 5 is formed of a parallel surface substantially parallel to the axial direction A.

Figure 6:
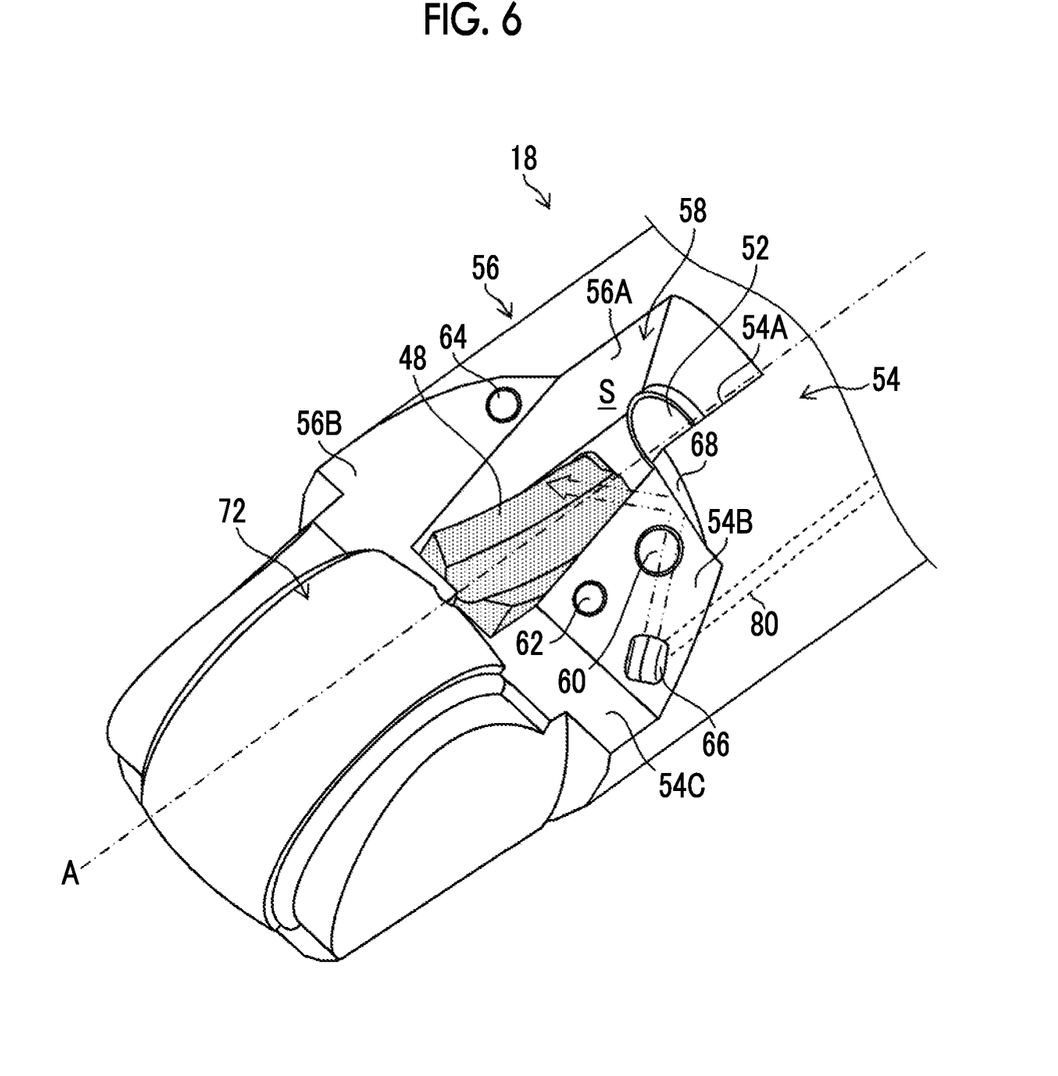
FIG. 6 is an enlarged perspective view of a distal-end-portion body of an endoscope according to a first modification example of the fourth embodiment.

FIG. 6 is an enlarged perspective view of a distal-end-portion body 18 of an endoscope 10 according to a first modification example of the fourth embodiment. As shown in FIG. 6, an ultrasound probe 72 is disposed on the distal end side of a distal-end-portion body 18. The distal-end-portion body 18 of the first modification example includes a treatment tool outlet 52, a space S that forms a standing base-housing portion, a standing base 48 that is housed in the space S, and a pair of walls 54 and 56 that include wall surfaces 54A and 56A for forming the space S. The space S includes an opening 58, and is opened toward the ultrasound probe 72 through the opening 58 in a case in which the distal-end-portion body 18 is viewed from the distal end side.

The wall 54 includes a flat surface 54B that is continuously connected to the wall surface 54A, and a flat surface 54C that is continuously connected to the flat surface 54B and extends to the distal end side. Further, the wall 56 includes a flat surface 56B that is continuously connected to the wall surface 56A. In the first modification example, the flat surfaces 54B and 56B are formed of inclined surfaces that are inclined with respect to the axial direction A. The flat surface 54C is formed of a parallel surface parallel to the axial direction A. The first modification example of the fourth embodiment forms an oblique-viewing endoscope.

The flat surfaces 54B and 56B are inclined so as to get close to the proximal end side as the flat surfaces 54B and 56B are spaced apart from the flat surface 54C. A nozzle 66, an observation window 60, and a guide wall 68 are arranged on the flat surface 54B along the ejection direction of washing water toward the proximal end side from the distal end side. The guide wall 68 is disposed at a position facing the nozzle 66 with the observation window 60 interposed therebetween. The nozzle 66 is disposed on the distal end side of the distal-end-portion body 18, and is adapted to eject washing water toward the proximal end side.

An illumination window 62 is disposed on the flat surface 54B at a position corresponding to substantially the same height as the nozzle 66 from the flat surface 54C used as a reference. Further, an illumination window 64 is disposed on the flat surface 56B at a position higher than the illumination window 62 disposed on the flat surface 54B from the flat surface 54C used as a reference.

Figure 7:
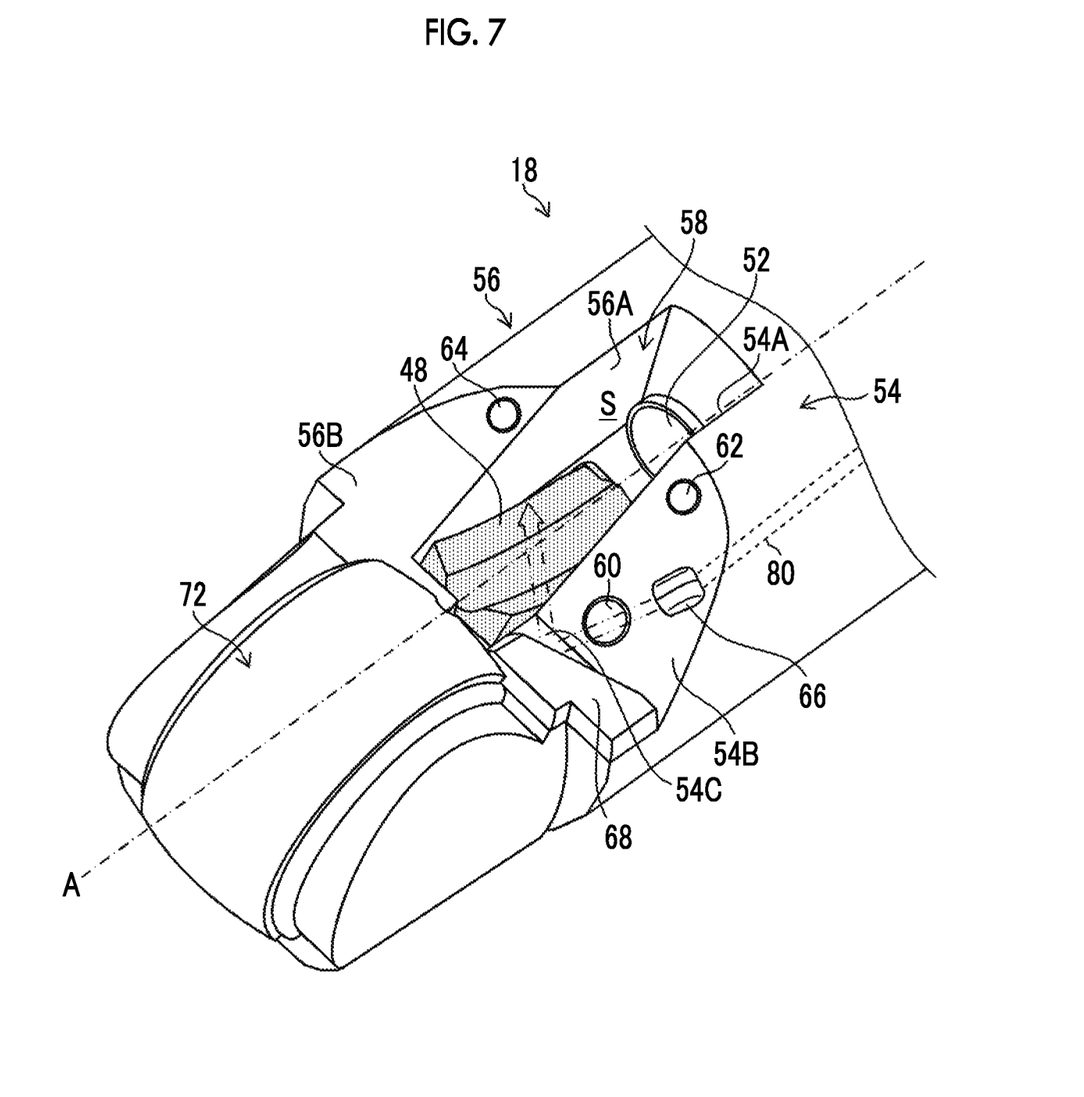
FIG. 7 is an enlarged perspective view of a distal-end-portion body of an endoscope according to a second modification example of the fourth embodiment.

FIG. 7 is an enlarged perspective view of a distal-end-portion body 18 of an endoscope 10 according to a second modification example of the fourth embodiment. The endoscope according to the second modification example has the same structure as the endoscope according to the first modification example except for the arrangement of an observation window 60, a nozzle 66, and a guide wall 68.

In the second modification example, a guide wall 68, an observation window 60, a nozzle 66, and an illumination window 62 are arranged in this order toward the proximal end side from the distal end side. The guide wall 68, the observation window 60, and the nozzle 66 are arranged along the ejection direction of washing water. The guide wall 68 is disposed at a position facing the nozzle 66 with the observation window 60 interposed therebetween. Further, the guide wall 68 is disposed on a flat surface 54C, and the observation window 60 and the nozzle 66 are disposed on a flat surface 54B that is an inclined surface. The second modification example of the fourth embodiment forms an oblique-viewing endoscope.

Figure 8:
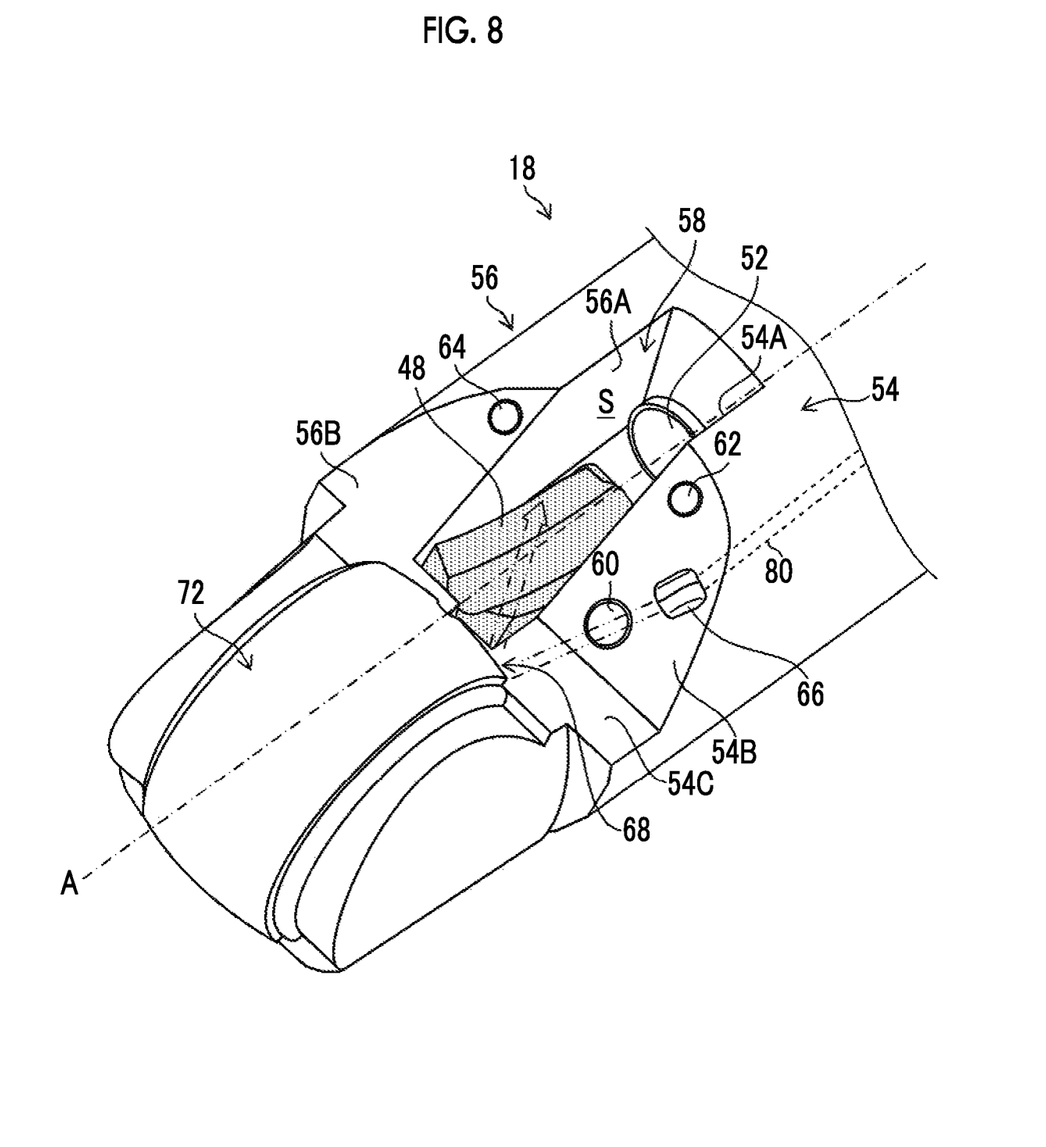
FIG. 8 is an enlarged perspective view of a distal-end-portion body of an endoscope according to a third modification example of the fourth embodiment.

FIG. 8 is an enlarged perspective view of a distal-end-portion body 18 of an endoscope 10 according to a third modification example of the fourth embodiment. The endoscope according to the third modification example has the same structure as the endoscope according to the second modification example except for the arrangement of a guide wall 68.

In the endoscope according to the third modification example, an observation window 60, a nozzle 66, and an illumination window 62 are disposed toward the proximal end side from the distal end side of a flat surface 54B. In the third modification example, the proximal end side of an ultrasound probe 72 functions as a guide wall 68. The proximal end side of the ultrasound probe 72, the observation window 60, and the nozzle 66 are arranged along the ejection direction of washing water. The proximal end side of the ultrasound probe 72, which is a guide wall 68, is disposed at a position facing the nozzle 66 with the observation window 60 interposed therebetween. The proximal end side of the ultrasound probe 72, which is the guide wall 68, guides washing water to a space S.

Next, the action of the structure will be described. As shown in FIGS. 5 to 8, even in an endoscope including ultrasound transducers, washing water is ejected toward the observation window 60 from the nozzle 66 provided on the flat surface 54B as shown by an arrow by the operation of the air/water supply button 32 of the operation unit 14. Washing water, which has passed the surface of the observation window 60, collides with the guide wall 68. Washing water, which has collided with the guide wall 68, is guided to the space S, which is a standing base-housing portion, by the guide wall 68 and is guided toward the standing base 48. The standing base 48 is washed with washing water.

Washing water, which flows into the space S, is sucked from the treatment tool outlet 52 by the operation of the suction button 34 of the operation unit 14 and is removed from the space S. The inside of the treatment tool channel can be washed with washing water that is sucked from the treatment tool outlet 52.

Washing water adhering to the observation window 60 can be blown off by gas to be ejected from the nozzle 66.

Fifth Embodiment

An endoscope according to a fifth embodiment will be described with reference to FIG. 9. There is a case where the same components as the components of the endoscopes 10 according to the first to fourth embodiments are denoted by the same reference numerals as the reference numerals of the first to fourth embodiments and the description thereof are omitted. An endoscope 10 shown in FIG. 9, which is the endoscope according to the fifth embodiment, is a side-viewing endoscope used as, for example, a duodenoscope and a distal-end-portion body 18 shown in FIG. 9 shows the structure of the side-viewing endoscope.

Figure 9:
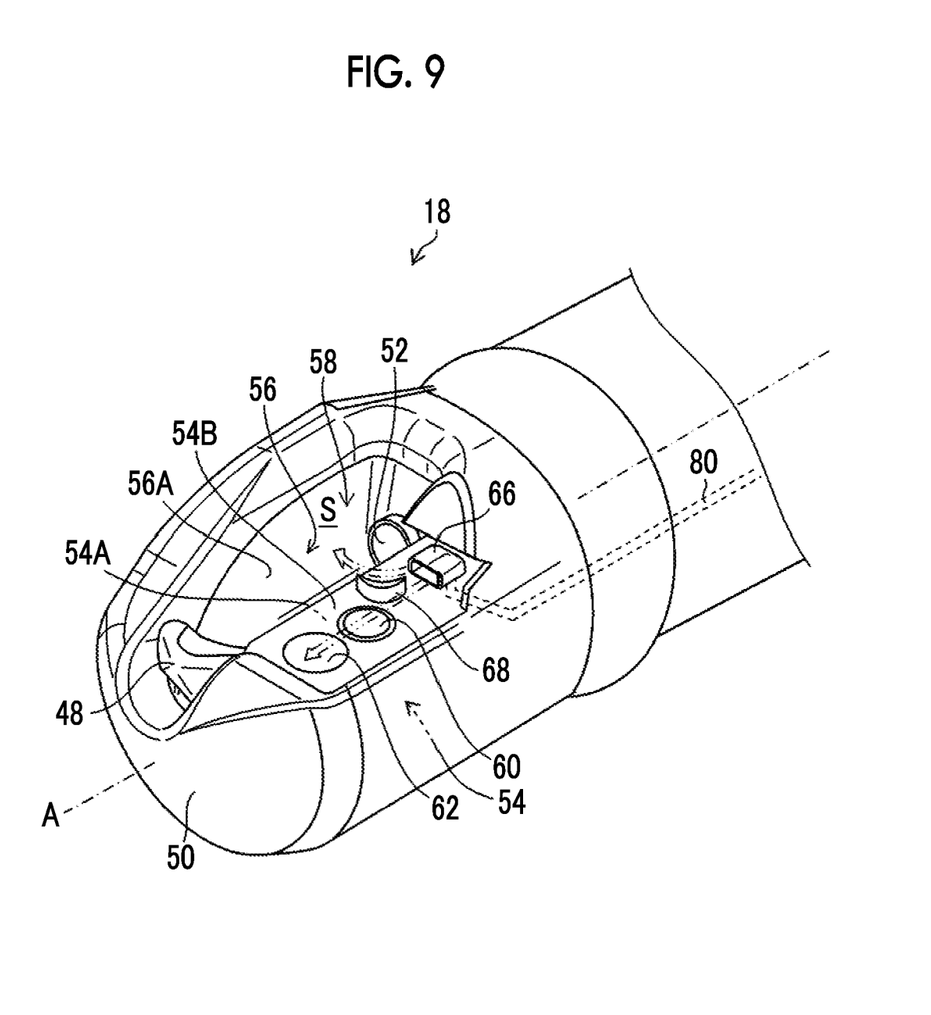
FIG. 9 is an enlarged perspective view of a distal-end-portion body of an endoscope according to a fifth embodiment.

As shown in FIG. 9, the distal-end-portion body 18 includes a treatment tool outlet 52 that is provided on the proximal end side thereof. A space S, which forms a standing base-housing portion, is formed by a pair of walls 54 and 56 that includes wall surfaces 54A and 56A facing each other and is disposed so as to be spaced apart from each other. The space S is adjacent to the treatment tool outlet 52. A standing base 48 is disposed on the front side of the treatment tool outlet 52 so as to be spaced apart from the treatment tool outlet 52, and is housed in the space S. An opening 58 is formed in the space S, and the space S is opened toward a standing position of the standing base 48 through the opening 58. In the fifth embodiment shown in FIG. 9, the standing base 48 is in a state in which the standing base 48 is in a falling position. Further, the distal-end-portion body 18 is covered with a cap 50.

As in the endoscope according to the first embodiment, in the endoscope according to the fifth embodiment shown in FIG. 9, an illumination window 62, an observation window 60, and a nozzle 66 are arranged toward the proximal end side from the distal end side on a flat surface 54B, which is a parallel surface of the distal-end-portion body 18, so as to be substantially parallel to an axial direction A.

The endoscope according to the fifth embodiment is different from the endoscope according to the first embodiment in terms of a position at which a guide wall 68 is disposed. In the endoscope according to the fifth embodiment, the guide wall 68 is disposed between the observation window 60 and the nozzle 66. The guide wall 68 is disposed at a position where a part of washing water to be ejected from the nozzle 66 collides with the guide wall 68 and allows the rest of the washing water to pass.

Next, the action of the structure will be described. As shown in FIG. 9, washing water is ejected toward the observation window 60 and the illumination window 62 from the nozzle 66 provided on the flat surface 54B as shown by an arrow by the operation of the air/water supply button 32 of the operation unit 14. The guide wall 68 is disposed between the observation window 60 and the nozzle 66. A part of washing water collides with the guide wall 68 before reaching the observation window 60. Washing water, which has collided with the guide wall 68, is guided to the space S by the guide wall 68 and is guided toward the standing base 48. The standing base 48 is washed with washing water. How much washing water is to be guided to the space S before washing water reaches the observation window 60 can be appropriately determined depending on a position at which the guide wall 68 is disposed.

As long as the guide wall 68 can guide a part of washing water to the space S before washing water reaches the observation window 60, the shape of the guide wall 68 is not particularly limited. The guide wall 68 may have a linear shape in top view, and may have the shape of a curve, such as the shape of an arc shape, the shape of an elliptical arc, or the shape of a parabola in top view. In a case in which the guide wall 68 has the shape of a curve, it is preferable that the guide wall 68 is disposed so that the nozzle 66 is positioned inside the curved guide wall 68. The guidance of washing water, which has passed the observation window 60, to the side opposite to the space S can be suppressed.

Washing water, which flows into the space S, is sucked from the treatment tool outlet 52 by the operation of the suction button 34 of the operation unit 14 and is removed from the space S. The inside of the treatment tool channel can be washed with washing water that is sucked from the treatment tool outlet 52.

The rest of the washing water, which does not collide with the guide wall 68, passes the surface of the observation window 60 and the surface of the illumination window 62, and washes the surface of the observation window 60 and the surface of the illumination window 62. Washing water flows out of the distal-end-portion body 18 along the flat surface 54B.

Washing water adhering to the observation window 60 can be blown off by gas to be ejected from the nozzle 66.

In the endoscope according to the fifth embodiment, the guide wall 68 is disposed between the observation window 60 and the nozzle 66. In addition, an additional guide wall can be provided on the flat surface 54B. For example, in a case in which an additional guide wall is provided closer to the distal end side than the illumination window 62, washing water flowing out of the distal-end-portion body 18 can be efficiently guided to the space S.

The embodiments of the invention have been described on the basis of the first to fifth embodiments. However, the invention is not limited to these embodiments. For example, the guide wall of the fifth embodiment can also be applied to an ultrasonic endoscope. Accordingly, other combinations of the embodiments are allowed without departing from the invention.

EXPLANATION OF REFERENCES

- 10: endoscope
- 12: insertion part
- 14: operation unit
- 16: universal cord
- 18: distal-end-portion body
- 20: bendable portion
- 22: soft portion
- 28: angle knob
- 30: standing operation lever
- 32: air/water supply button
- 34: suction button
- 36: treatment tool insertion opening
- 48: standing base
- 50: cap
- 52: treatment tool outlet
- 54: wall
- 54A: wall surface
- 54B: flat surface
- 54C: flat surface
- 56: wall
- 56A: wall surface
- 56B: flat surface
- 58: opening
- 60: observation window
- 62: illumination window
- 64: illumination window
- 66: nozzle
- 68: guide wall
- 72: ultrasound probe
- 80: air/water supply pipe line
- 82: port
- 84: branch pipe line
- A: axial direction
- S: space

What is claimed is:

1. An endoscope comprising:
    an insertion part that includes a distal end and a proximal end; and
    a distal-end-portion body that is provided on a distal end side of the insertion part and formed with a treatment tool outlet from which a treatment tool is led out,
    wherein the distal-end-portion body includes an observation window, a nozzle that ejects washing water to the observation window, a standing base that is disposed in a standing base-housing portion adjacent to the treatment tool outlet and is rotationally moved between a standing position and a falling position, and a guide wall that is disposed at a position facing the nozzle with the observation window interposed therebetween and guides the washing water to be ejected from the nozzle to the standing base-housing portion,
    wherein the standing base-housing portion is formed by a pair of walls including wall surfaces facing each other with the standing base interposed therebetween, one wall of the pair of walls includes a flat surface continuously connected to the wall surface of the one wall, and the observation window and the nozzle are disposed on the flat surface,
    wherein the flat surface is formed of an inclined surface that is inclined with respect to an axial direction of the distal-end-portion body.

2. An endoscope comprising:
    an insertion part that includes a distal end and a proximal end; and
    a distal-end-portion body that is provided on a distal end side of the insertion part and formed with a treatment tool outlet from which a treatment tool is led out,
    wherein the distal-end-portion body includes an observation window, a nozzle that ejects washing water to the observation window, a standing base that is disposed in a standing base-housing portion adjacent to the treatment tool outlet and is rotationally moved between a standing position and a falling position, and a guide wall that is disposed between the observation window and the nozzle and guides a part of the washing water to be ejected from the nozzle to the standing base-housing portion,
    wherein the standing base-housing portion is formed by a pair of walls including wall surfaces facing each other with the standing base interposed therebetween, one wall of the pair of walls includes a flat surface continuously connected to the wall surface of the one wall, and the observation window and the nozzle are disposed on the flat surface,
    wherein the flat surface is formed of an inclined surface that is inclined with respect to an axial direction of the distal-end-portion body.

3. The endoscope according to claim 1,
    wherein the guide wall is disposed on the flat surface.

4. The endoscope according to claim 2,
    wherein the guide wall is disposed on the flat surface.

5. The endoscope according to claim 1,
    wherein the nozzle is disposed closer to a distal end side of the distal-end-portion body than the observation window and ejects the washing water toward a proximal end side of the distal-end-portion body.

6. The endoscope according to claim 2,
    wherein the nozzle is disposed closer to a distal end side of the distal-end-portion body than the observation window and ejects the washing water toward a proximal end side of the distal-end-portion body.

7. The endoscope according to claim 1, further comprising:
    an ultrasound transducer that is provided on a distal end side of the distal-end-portion body.

8. The endoscope according to claim 2, further comprising:
    an ultrasound transducer that is provided on a distal end side of the distal-end-portion body.

9. The endoscope according to claim 1, further comprising:
- a port that is provided on the wall surface of the one wall and ejects the washing water; and
- a branch pipe line that connects a fluid pipe line connected to the nozzle to the port.

10. The endoscope according to claim 2, further comprising:
- a port that is provided on the wall surface of the one wall and ejects the washing water; and
- a branch pipe line that connects a fluid pipe line connected to the nozzle to the port.

11. The endoscope according to claim 9,
wherein the wall surface of the other wall is positioned on an extension of an ejection direction of the washing water to be ejected from the port in a state in which the standing base is in the falling position.

12. The endoscope according to claim 10,
wherein the wall surface of the other wall is positioned on an extension of an ejection direction of the washing water to be ejected from the port in a state in which the standing base is in the falling position.

* * * * *